United States Patent [19]

Burns et al.

[11] Patent Number: 5,290,901
[45] Date of Patent: Mar. 1, 1994

[54] METHOD FOR PREPARATION OF CARBINOL-FUNCTIONAL SILOXANES

[75] Inventors: Gary T. Burns; Gary T. Decker; Aroop K. Roy, all of Midland, Mich.

[73] Assignee: Dow Corning Corporation, Midland, Mich.

[21] Appl. No.: 74,512

[22] Filed: Jun. 14, 1993

[51] Int. Cl.$^5$ .............................................. C08G 77/04
[52] U.S. Cl. ....................................... 528/34; 528/37; 556/450; 556/466
[58] Field of Search ................... 528/37, 34; 556/450, 556/466

[56] References Cited

U.S. PATENT DOCUMENTS 5,223,596  6/1993  Okawa et al. ......................... 528/37

Primary Examiner—Melvyn I. Marquis
Attorney, Agent, or Firm—William F. Boley

[57] ABSTRACT

The present invention is a method for the preparation of carbinol-functional organosiloxanes and carbinol-functional organosiloxane resins. The method comprises contacting a cyclic silyl ether with an organosiloxane or an organosiloxane resin at a temperature within a range of about 25° C. to 150° C. The method may be conducted in the presence of an inert organic solvent to facilitate dissolution and contact of the reactants.

25 Claims, No Drawings

METHOD FOR PREPARATION OF CARBINOL-FUNCTIONAL SILOXANES

BACKGROUND OF INVENTION

The present invention is a method for the preparation of carbinol-functional organosiloxanes and carbinol functional organosiloxane resins. The method comprises contacting a cyclic silyl ether with an organosiloxane or an organosiloxane resin at a temperature within a range of about 25° C. to 150° C. The method may be conducted in the presence of an inert organic solvent to facilitate dissolution and contact of the reactants.

Several methods for preparation of cyclic silyl ethers useful in the present invention have been described. For example, Knoth et al., J. Am. Chem. Soc. 80:4106, 1958, describe the preparation of various 2,2-disubstituted 1-oxa-2-silacycloalkanes by heating the corresponding (chloroalkyoxy)chlorosilanes with metallic sodium or lithium. Knoth et al. further report that the cyclic silyl ethers can be hydrolyzed to form the corresponding bis(hydroxyalkyl)tetraalkyldisiloxanes. Speir et al.. J. Org. Chem. 25:1637, 1960, teach that 1,3-bis(hydroxypropyl) tetramethyldisiloxane prepared by the methanolysis of 1,3-bis(acetoxypropyl)tetramethyldisiloxane loses water during distillation to form 2,2-dimethyl-1-oxa-2-silacyclopentane. Speir et al. further teach that the equilibrium can be shifted in favor of the cyclic silyl ether by use of a drying agent such as lime during the distillation process. Knoth. U.S. Pat. No. 2,983,744, issued May 9, 1961, describes a process for the production of cyclic silyl ethers, the process involving reacting with two equivalents of an alkali metal or alkaline earth metal an omega-halogenoalkoxydihydrocarbohalogenosilane. Knoth further reports that the 2,2-dihydrocarbo-1-oxa-2-silacycloalkanes prepared by the described method are readily converted by hydrolysis to long chain oxadisila-alpha,omega-diols. Berger, U.S. Pat. No. 3,505,380, issued Apr. 7. 1970, describes a hydrosilation process for preparing cyclic silyl ethers, the process comprising contacting in the presence of platinum catalyst a mixture of an unsaturated silicon hydride, unsaturated silicon compound, and silicon hydride. Chen et al., Organometallics 6:2590, 1987, teach the preparation of cyclic silyl ethers by adding triphenylmethyl perchlorate to a methylene chloride solution of the corresponding silyl hydride.

All of the above described methods are useful for making cyclic silyl ethers useful in the present claimed method. However, a preferred method is described by Mironov et al., Zhurnal Obshchei Khimii 39:966, 1969. Mironov et al. teach that (methallyloxy)dimethylsilane in the presence of a platinum catalyst can undergo an intramolecular hydrosilation reaction to form the corresponding 1-oxa-2-silacycloalkane.

Gol'din et al., Zhurnal Obshchei Khimii 45:2451, 1975, teach a process for the preparation of carbofunctional siloxanes. The process involves the reaction of cyclosiloxanes with carbofunctional disiloxanes containing hydroxy-, carboxy-, acyloxy-, or cyano-terminal groups in the presence of a catalytic ion-exchange resin.

The present invention is a method which can yield a near quantative yield of carbinol-functional organosiloxanes and carbinol-functional organosiloxane resins. The method does not require a catalyst and can be conducted by contacting a cyclic silyl ether with an organosiloxane or an organo siloxane resin at a temperature within a range of about 25° C. to 150° C.

Carbinol-functional organosiloxanes and carbinol-functional organosiloxane resins prepared by the present method may be useful, for example, to form silicone and urethane copolymers, and to modify organic resins, coatings, paints, foams, and elastomers.

SUMMARY OF INVENTION

The present invention is a method for the preparation of carbinol-functional organosiloxanes and carbinol-functional organosiloxane resins. The method comprises contacting a cyclic silyl ether with an organosiloxane or an organosiloxane resin at a temperature within a range of about 25° C. to 150° C. The method may be conducted in the presence of an inert organic solvent to facilitate dissolution and contact of the reactants.

DESCRIPTION OF INVENTION

The present invention is a method for preparation of carbinol-functional organosiloxanes described by formula

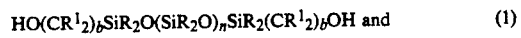

$$HO(CR^1_2)_bSiR_2O(SiR_2O)_nSiR_2(CR^1_2)_bOH \text{ and} \qquad (1)$$

carbinol-functional organosiloxane resins described by formula

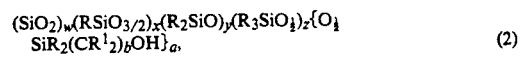

$$(SiO_2)_w(RSiO_{3/2})_x(R_2SiO)_y(R_3SiO_{\frac{1}{2}})_z\{O_{\frac{1}{2}}SiR_2(CR^1_2)_bOH\}_a, \qquad (2)$$

the method comprising: contacting a cyclic silyl ether described by formula

$$R_2Si-O(CR^1_2)_b \qquad (3)$$

with an organosiloxane described by formula

$$HO(R_2SiO)_nH \qquad (4)$$

or an organosiloxane resin described by formula

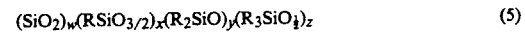

$$(SiO_2)_w(RSiO_{3/2})_x(R_2SiO)_y(R_3SiO_{\frac{1}{2}})_z \qquad (5)$$

at a temperature within a range of about 25° C. to 150° C.; where each R is independently selected from a group consisting of alkyls comprising one to 20 carbon atoms, cycloalkyls comprising three to 20 carbon atoms, alkenyls comprising two to 20 carbon atoms, aralkyls, and aryls; each $R^1$ is independently selected from a group consisting of hydrogen, R, and substituted hydrocarbyls comprising one to 20 carbon atoms: $b=3$, 4, or 5; $n=1$ to 15,000; the values w, x, y, and z are mole percents, $w<100$, $w+x>0$, and $w+x+y+z=100$; and the organosiloxane resin comprises 0.1 to 15 weight percent silanol, the value a represents the proportion of the silanol substituted with carbinol functional silyl, and $a>0$.

The present method involves the contact of a cyclic silyl ether described by formula (3) with an organosiloxane described by formula (4) or an organosiloxane resin described by formula (5). The method of contact is not critical to the present invention and can be those generally known in the art for contacting mixtures of liquids or for contacting mixtures of liquids and solids. It is generally preferred that the cyclic silyl ether be added to the organosiloxane or organosiloxane resin at about the rate the cyclic silyl ether is being consumed by the resultant reaction.

An inert organic solvent may be used in the method to facilitate contact of the cyclic silyl ether and the organosiloxane or organosiloxane resin. Suitable examples of such inert organic solvents include the normally liquid aliphatic hydrocarbons such as the pentanes, hexanes, heptanes, octanes, and decanes; the normally liquid aromatic hydrocarbons such as benzene, toluene, and xylene; and hydrocarbon ethers such as diethyl ether and dibutyl ether. The amount of inert organic solvent suitable for use in the present invention can be that which provides for adequate solubilization and dilution of the reactants to facilitate their contact. The inert organic solvent can also act as a refluxing aid in the method.

Cyclic silyl ethers useful in the present method are described by formula (3). In formula (3) the value of b can be three, four, or five. The preferred value for b is three.

In formula (3), each R is independently selected from a group consisting of alkyls comprising one to 20 carbon atoms. cycloalkyls comprising three to 20 carbon atoms, alkenyls comprising two to 20 carbon atoms aralkyls, and aryls. The substituent R can be, for example, methyl, ethyl, propyl, isopropyl, butyl, tert-butyl, pentyl, cyclopropyl, cyclopentyl, vinyl, allyl, hexenyl benzyl, beta-phenylethyl, gamma-tolylpropyl, phenyl, tolyl, xylyl, and naphthyl. Preferred is when each R is independently selected from a group consisting of methyl, vinyl, and phenyl. Most preferred is when all substituents R are methyl.

The cyclic silyl ethers useful in the present method have substituents $R^1$, where each $R^1$ is independently selected from a group consisting of hydrogen, R, and substituted hydrocarbyls comprising one to 20 carbon atoms. The substituent $R^1$ can be, for example, hydrogen, R as previously described, 3,3,3-trifluoropropyl, and perfluoropropyl. Preferred is when each $R^1$ is independently selected from a group consisting of hydrogen, methyl, vinyl, phenyl, and 3,3,3-trifluoropropyl. Most preferred is when each $R^1$ is independently selected from a group consisting essentially of hydrogen and methyl.

The method of preparing the cyclic silyl ethers useful in the present method is not critical to the present method and can be those, for example, as described in the Background Section herein. A preferred method for preparing the cyclic silyl ether is by the intramolecular hydrosilation of an (alloxy)diorganohydrosilane in the presence of a platinum catalyst. Such a process is described in the Examples provided herein and in Mironov et al., Zhurnal Obshchei Khimii 39:966. 1969. It is preferred that the cyclic silyl ether be freshly distilled prior to use, since this results in improved yield of the carbinol-functional organosiloxanes and carbinol-functional organosiloxane resins.

The cyclic silyl ether can be, for example, 2,2,4- trimethyl-1-oxa-2-silacyclopentane 2,2-dimethyl-1-oxa-2-silacyclopentane, 2,2-diphenyl-1-oxa-2-silacyclopentane, 2,2-dimethyl-3-phenyl-1-oxa-2-silacyclopentane, and 2,2-dimethyl-1-oxa-2-silacyclohexane. The preferred cyclic silyl ether is 2,2,4-trimethyl-1-oxa-2-silacyclopentane.

The amount of cyclic silyl ether employed in the present method will depend upon the amount of hydroxyl functionality present on the organosiloxane or organosiloxane resin and the amount of this hydroxyl functionality it is desired to replace with carbinol functionality. Generally, it is preferred that the present method be conducted with about a one percent to a 50 percent stoichiometric excess of cyclic silyl ether in relation to hydroxyl functionality present on the organosiloxane or the organosiloxane resin. More preferred is when the present method is conducted with about a 5 percent to a 20 percent stoichiometric excess of cyclic silyl ether in relation to hydroxyl functionality present on the organosiloxane or the organosiloxane resin.

The cyclic silyl ether is contacted with an organosiloxane as described by formula (4) or an organosiloxane resin as described by formula (5). The organosiloxane contains substituents R, where R is as previously described for the cyclic silyl ether.

The number of siloxy units, i.e. —$R_2SiO$—, present in the organosiloxane is represented in formula (4) by the designation n, where n is a value within a range of one to 15,000. Preferred is when n is a value within a range of one to 100. Those skilled in the art will recognize that the organosiloxane can be a monodispersed polymer in which case n is an integer within the described ranges, or the organosiloxane can be a mixture of organosiloxanes having different degrees of polymerization in which case n is an average value within the described ranges.

The organosiloxane resin contains substituents R, where R is as previously described for the cyclic silyl ether. The organosiloxane resin can be comprised of four components, as designated in formula (5), where the mole percents of the components present in the organosiloxane resin are represented by the subscript values w, x, y, and z. In formula (5) the mole percent (w) of the $SiO_2$ component must be less than 100. In addition to provide for the branched structure characteristic of the organosiloxane resin, the sum of the mole percents of $SiO_2$ and $RSiO_{3/2}$ must be greater than zero, i.e, $w+x>0$. Preferred are those organosiloxane resins where $5<w+x<90$.

For the present method to be effective the organosiloxane resin must contain hydroxyl functionality in the form of silanol i.e. SiOH. The silanol can comprise any value greater than zero weight percent to about 30 weight percent of the organosiloxane resin. Preferred is when the silanol comprises about 0.1 weight percent to 15 weight percent of the organosiloxane resin.

The present method can be conducted at a temperature within a range of about 25° C. to 150° C. Preferred is when the method is conducted at a temperature within a range of about 50° C. to 130° C. The present method can be conducted at the reflux temperature of the liquid mixture present in the method.

The carbinol-functional organosiloxanes which can be prepared by the present method are described by formula (1), where R, $R^1$ and n are as previously described. Typically the present method yields a near quantative yield of the carbinol functional organosiloxane. However depending on the particular cyclic silyl ether and organosiloxane used and, if used, the presence of solvent, it may be desirable to effect further separation of the carbinol-functional organosiloxane from unreacted feed materials, byproducts, and solvents. Such separations can be effected by standard means for effecting such separations, for example, distillation.

Carbinol-functional organosiloxane resins which can be prepared by the present method are described by formula (2). where R, $R^1$, w, x, y, and z are as previously described. In formula (2), the value a represents the proportion of silanol initially present in the organosiloxane resin that is substituted with the carbinol functionality. Therefore, a can be any value greater than zero percent up to and including 100 percent of the silanol present in the organosiloxane resin. If required, the carbinol-functional organosiloxane resin can be further separated from unreacted feed materials, by-products, and solvents by standard means, for example, distillation.

The following examples are provided to illustrate the present method. These examples are not intended to limit the scope of the claims herein.

EXAMPLE 1 (Not within the scope of the present invention)

The synthesis of 2,2,4-trimethyl-1-oxa-2-silacyclopentane was conducted. A 500 mL flask equipped with a magnetic stirring bar, dropping funnel, and reflux condenser was purged with nitrogen. Into the purged flask was added 42.9 mL of 2-methyl-2-propene-1-ol. Then 45.8 mL of 1,1,3,3-tetramethyldisilazane was added to the stirred alcohol over a 10 to 15 minute period while maintaining the temperature of the resultant mixture at 25° C. After 30 minutes of stirring, the mixture was heated for one hour at 80° C. to 90° C. The mixture was then cooled and distilled to provide a 82% yield of a material identified by $^{13}C$ NMR as methallyloxydimethylsilane, i.e. $CH_2=CHMeCH_2OSiMe_2H$.

A flask similar to that previously described was then charged with a chloroplatinic acid solution (1.6 mL of 10% w/V $H_2PtCl_6 \cdot xH_2O$ in 2-propanol). The previously prepared methallyloxydimethylsilane was added to the chloroplatinic acid solution over a one hour period while maintaining a gentle reflux of the mixture in the flask. The flask temperature was raised to 125° C. to 130° C. during the addition of the methallyoxydimethylsilane and maintained there for 3.0 to 3.5 hours. During the course of this time, the mixture became extremely viscous and was virtually not stirrable. After cooling the flask to room temperature, the mixture was distilled with the initial distillation occurring at 120° C., to 135° C. followed by a slight fall in the temperature and the rapid exothermic cracking of the high polymer. Distillation was continued at a temperature within a range of 130° C. to 180° C. until completion. Analysis of the resulting product by $^{13}C$ NMR and $^{29}Si$ NMR demonstrated a 77 percent yield of 2,2,4-trimethyl-1-oxa-2-silacyclopentane.

EXAMPLE 2

The reaction of 1,1,3,3-tetramethyldisiloxanediol with 2,2,4-trimethyl-1-oxa-2-silacyclopentane was evaluated. The reactor consisted of a 25 mL flask equipped with a magnetic stirring bar and having a gas inlet. The reactor was purged with nitrogen and then charged with 0.49 g of 1,1,3,3-tetramethyldisiloxanediol. Then 0.78 g of 2,2,4-trimethyl-1-oxa-2-silacyclopentane (prepared as described in Example 1) was quickly added to the flask. This mixture was heated for 2 hours at 60° C. to 65° C. After cooling to room temperature, examination of the flask contents by $^1H$ and $^{29}Si$ NMR showed pure $O(SiMe_2O)_2(SiMe_2CH_2 CHMeCH_2OH)_2$.

EXAMPLE 3

The reaction of 1,3-diphenyl-1,3-dimethyldisiloxanediol with 2,2,4-trimethyl-1-oxa-2-silacyclopentane was evaluated. The process was conducted in a reactor similar to that described in Example 2. The reactor was purged with nitrogen and then charged with 7.25 g of 1,3-diphenyl-1,3-dimethyldisiloxandiol and 7.8 g of 2,2,4-trimethyl-1-oxa-2-silacyclopentane (prepared as described in Example 1). This mixture was heated for one hour at 80° C. to 85° C. and then for 3.5 hours at 70° C. The resulting mixture was stripped at 70° C. to remove excess unreacted 2,2,4-trimethyl-1-oxa-2-silacyclopentane. The stripped product was analyzed by $^{29}Si$ NMR and found to be 95 percent pure $O(OSiMePh)_2$-$(SiMe_2CH_2CHMeCH_2OH)_2$.

EXAMPLE 4

The reaction of diphenylsilanediol with 2,2,4-trimethyl-1-oxa-2-silacyclopentane was evaluated. A reaction flask similar to that described in Example 2 was equipped with a reflux condenser. A mixture was formed in the flask comprising 15 mL anhydrous toluene, 7.15 g of 2,2,4-trimethyl-1-oxa-2-silacyclopentane, and 5.4 g of diphenylsilanediol. The diphenylsilanediol was dissolved by heating the mixture to a temperature of 105° C. to 117° C. After the diphenylsilanediol dissolved the mixture was heated at 120° C. for 2 hours, then stripped at 65° C. to 70° C. to remove excess toluene and 2,2,4-trimethyl-1-oxa-2-silacyclopentane. This resulted in a near quantative yield of $Ph_2Si(OSiMe_2CH_2CHMeCH_2OH)_2$.

EXAMPLE 5

The reaction of silanol endcapped dimethylpolysiloxane with 2,2,4-trimethyl-1-oxa-2-silacyclopentane was evaluated. The reaction was conducted in a 3000 mL flask equipped with a magnetic stirring bar and a dropping funnel and having a gas inlet. The flask was purged with nitrogen and charged with 1943 g of a dry silanol endcapped dimethylpolysiloxane with a dp of 33. The dimethylpolysiloxane was heated to 95° C. and then 226 g of 2,2,4-trimethyl-1-oxa-2-silacyclopentane was added from the dropping funnel over a 15 to 20 minute period. The mixture was heated at 95° C. for four hours. The mixture was then stripped at 80° C. for 1.5 hours to remove excess 2,2,4-trimethyl-1-oxa-2-silacyclopentane. The resultant stripped product was analyzed by $^{13}C$ NMR and $^{29}Si$ NMR and found to comprise a near quantitative yield of carbinol endcapped dimethylpolysiloxane.

EXAMPLE 6

The reaction of silanol endcapped (methyl-3,3,3-trifluoropropyl)polysiloxane with 2,2,4-trimethyl-1-oxa-2-silacyclopentane was evaluated. The reaction was conducted similar to that described for Example 5. A mixture comprising 39.24 g of silanol endcapped (methyl-3,3,3-trifluoropropyl)polysiloxane having a dp of 25 was formed with 2.73 g of 2,2,4-trimethyl-1-oxa-2-silacyclopentane. The mixture was stirred at room temperature for 18 hours. The mixture was then stripped at 35° C. to remove unreacted 2,2,4-trimethyl-1-oxa-2-silacyclopentane. The stripped mixture was analyzed by $^{29}Si$ NMR and found to comprise about 60 weight percent carbinol endcapped product, with the remainder being unreacted (methyl-3,3,3-trifluoropropyl)-polysiloxane.

EXAMPLE 7

The reaction of a siloxane resin with 2,2,4-trimethyl-1-oxa-2-silacyclopentane was evaluated. The reaction was conducted in a 100 mL flask equipped with a magnetic stirring bar and a dropping funnel and having a gas inlet. The flask was purged with nitrogen and then 30 mL of anhydrous toluene was added. Then 10 g of a dry siloxane resin having a Mn of 555 and containing 70/30 w/w PhSi/propylSi units and 6 weight percent silanol (SiOH) units was added to the flask and dissolved in the toluene. About 5.51 g of 2,2,4-trimethyl-1-oxa-2-silacyclopentane was added to the flask and the resultant mixture heated for three hours at 65° C. to 70° C. The product was stripped at 65° C. for two hours to remove toluene and excess 2,2,4-trimethyl-1-oxa-2-silacyclopentane. The stripped product was analyzed by $^{29}$Si NMR and found to comprise carbinol functional siloxane resin having an Mn of 612.

EXAMPLE 8

The reaction of silanol endcapped dimethypolysiloxane with 2,2-dimethyl-1-oxa-2-silacyclohexane was evaluated. The reaction was conducted in a 100 mL flask equipped with a magnetic stirring bar and a dropping funnel and having a gas inlet. The flask was purged with nitrogen and charged with 10 g of a dry silanol endcapped dimethylpolysiloxane with a dp of about 33. Then about 1.5 g of distilled 2,2-dimethyl-1-oxa-2-silacyclohexane (Petrarch systems, Bristol, Pa.) was added to the flask and the resultant mixture heated at 85° C. for three hours. The mixture was then stripped for 1.5 hours at a temperature of 60° to 65° C. to remove excess 2,2-dimethyl-1-oxa-2-silacyclohexane. The stripped product was analyzed by $^{29}$Si NMR and found to comprise a near quantitative yield of carbinol endcapped dimethylpolysiloxane.

We claim:

1. A method for preparation of carbinol-functional organosiloxanes described by formula

$$HO(CR^1{}_2)_bSiR_2O(SiR_2O)_nSiR_2(CR^1{}_2)_bOH,$$

the method comprising:
contacting a cyclic silyl ether described by formula

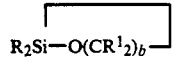

with an organosiloxane described by formula

$$HO(R_2SiO)_nH$$

at a temperature within a range of about 25° C. to 150° C.: where each R is independently selected from a group consisting of alkyls comprising one to 20 carbon atoms, cycloalkyls comprising three to 20 carbon atoms, alkenyls comprising two to 20 carbon atoms, aralkyls, and aryls; each $R^1$ is independently selected from a group consisting of hydrogen, R, and substituted hydrocarbyls comprising one to 20 carbon atoms; b=3, 4, or 5; and n=1 to 15,000.

2. A method according to claim 1, where b=3.

3. A method according to claim 1, where each R is independently selected from a group consisting of methyl, vinyl, and phenyl.

4. A method according to claim 1, where R is methyl.

5. A method according to claim 1, where each $R^1$ is independently selected from a group consisting of hydrogen, methyl, vinyl, phenyl, and 3,3,3-trifluoropropyl.

6. A method according to claim 1, where each $R^1$ is independently selected from a group consisting of hydrogen and methyl.

7. A method according to claim 1, where the cyclic silyl ether is 2,2,4-trimethyl-1-oxa-2-silacyclopentane.

8. A method according to claim 1, where the cyclic silyl ether is contacted with the organosiloxane at about a 5 mole percent to a 20 mole percent stoichiometric excess in relation to hydroxyl functionality present on the organosiloxane.

9. A method according to claim 1, where n is a value within a range of one to 100.

10. A method according to claim 1, where the temperature is within a range of about 50° C. to 130° C.

11. A method according to claim 1 further comprising the presence of an inert organic solvent.

12. A method according to claim 1, where the cyclic silyl ether is 2,2,4-trimethyl-1-oxa-2-silacyclopentane, the cyclic silyl ether is contacted with the organosiloxane at about a 5 mole percent to a 20 mole percent stoichiometric excess in relation to hydroxyl functionality present on the organosiloxane R, is methyl, n is a value within a range of one to 100, and the temperature is within a range of about 50° C. to 130° C.

13. A method for preparation of carbinol-functional organosiloxane resins described by formula

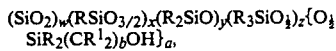

$$(SiO_2)_w(RSiO_{3/2})_x(R_2SiO)_y(R_3SiO_{\frac{1}{2}})_z\{O_{\frac{1}{2}}SiR_2(CR^1{}_2)_bOH\}_a,$$

the method comprising:
contacting a cyclic silyl ether described by formula

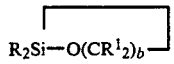

with an organosiloxane resin described by formula

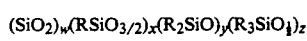

$$(SiO_2)_w(RSiO_{3/2})_x(R_2SiO)_y(R_3SiO_{\frac{1}{2}})_z$$

at a temperature within a range of about 25° C. to 150° C.; where each R is independently selected from a group consisting of alkyls comprising one to 20 carbon atoms, cycloalkyls comprising three to 20 carbon atoms, alkenyls comprising two to 20 carbon atoms, aralkyls, and aryls; each $R^1$ is independently selected from a group consisting of hydrogen, R, and substituted hydrocarbyls comprising one to 20 carbon atoms; b=3, 4, or 5; the values w, x, y, z are mole percents, w<100, w+x>0, and w+x+y+z=100; the organosiloxane resin comprises greater than zero weight percent silanol to about 30 weight percent silanol, and the value a represents the percent of the silanol substituted with carbinol functional silyl and a>0.

14. A method according to claim 13, where b=3.

15. A method according to claim 13, where each R is independently selected from a group consisting of methyl, vinyl, and phenyl.

16. A method according to claim 13, where R is methyl.

17. A method according to claim 13, where each $R^1$ is independently selected from a group consisting of hydrogen, methyl, vinyl, phenyl, and 3,3,3-trifluoropropyl.

18. A method according to claim 13, where each $R^1$ is independently selected from a group consisting of hydrogen and methyl.

19. A method according to claim 13, where the cyclic silyl ether is 2,2,4-trimethyl-1-oxa-2-silacyclopentane.

20. A method according to claim 13, where the cyclic silyl ether is contacted with the organosiloxane resin at about a 5 percent to a 20 percent stoichiometric excess in relation to hydroxyl functionality present on the organosiloxane resin.

21. A method according to claim 13, where the temperature is within a range of about 50° C. to 130° C.

22. A method according to claim 13, where $5<w+x<90$.

23. A method according to claim 13 further comprising the presence of an inert organic solvent.

24. A method according to claim 13, where the cyclic silyl ether is 2,2,4-trimethyl-1-oxa-2-silacyclopentane, the cyclic silyl ether is contacted with the organosiloxane resin at about a 5 mole percent to a 20 mole percent stoichiometric excess in relation to hydroxyl functionality present on the organosiloxane resin, the hydroxyl functionality as silanol comprises about 0.1 weight percent to 15 weight percent of the organosiloxane resin, R is methyl, $5<w+x<90$, and the temperature is within a range of about 50° C. to 130° C.

25. A method according to claim 13, where the silanol comprises about 0.1 weight percent to 15 weight percent on the organosiloxane resin.

* * * * *